United States Patent [19]

Hadley et al.

[11] 4,346,089
[45] Aug. 24, 1982

[54] 1-AZA-4-OXA-BICYCLO [4,4,0]DECANE DERIVATIVES

[75] Inventors: Michael S. Hadley, Sawbridgeworth; Francis D. King, Newport; Roger T. Martin, Harlow, all of England

[73] Assignee: Beecham Group Limited, England

[21] Appl. No.: 229,191

[22] Filed: Jan. 28, 1981

[30] Foreign Application Priority Data

Jan. 30, 1980 [GB] United Kingdom ................. 8003154
Sep. 6, 1980 [GB] United Kingdom ................. 8028864

[51] Int. Cl.³ .................. A61K 31/535; C07D 265/36
[52] U.S. Cl. .............................. 424/248.52; 424/246; 424/248.54; 544/105; 544/51; 544/52; 260/330
[58] Field of Search ................... 544/105; 424/248.52, 424/248.54

[56] References Cited

FOREIGN PATENT DOCUMENTS 2748260 5/1978 Fed. Rep. of Germany .

Primary Examiner—John M. Ford
Attorney, Agent, or Firm—Jacobs & Jacobs

[57] ABSTRACT

Compounds of the formula (I):

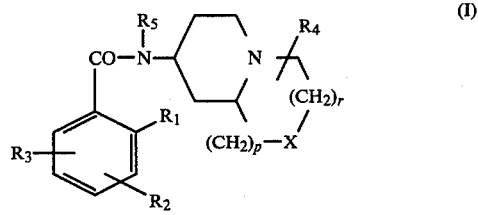

and pharmaceutically acceptable salts and N-oxides thereof, wherein:

$R_1$ is a $C_{1-6}$ alkoxy group;

$R_2$ and $R_3$ are the same or different and are hydrogen, halogen, $CF_3$, $C_{1-7}$acyl, $C_{1-7}$ acylamino, $C_{1-6}$ alkyl-$S(O)_n$ wherein n is 0, 1 or 2, nitro, $C_{1-6}$ alkoxy, hydroxy, or amino, aminocarbonyl or aminosulphonyl optionally substituted by one or two $C_{1-6}$ alkyl groups;

or $R_1$ and $R_2$ taken together are methylenedioxy or ethylenedioxy in which case $R_3$ is any one of the groups given for $R_1$ and $R_2$ above;

$R_4$ is hydrogen, $C_{1-4}$ alkyl, phenyl or phenyl $C_{1-4}$ alkyl;

$R_5$ is hydrogen or $C_{1-4}$alkyl;

X is an oxygen or sulphur atom; or a sulphoxide group $>S\sim O$;

p is 1 or 2; and r is 1 or 2; are useful in the treatment of disorders related to imparied gastrointestinal motility.

9 Claims, No Drawings

1-AZA-4-OXA-BICYCLO [4,4,0]DECANE DERIVATIVES

This invention relates to a group of novel compounds, their formulation as pharmaceutical compositions, and their use in the therapy of disorders.

West German Offenlegungsschrift No: 2,748,260.6 describes compounds of the formula (A), and pharmaceutically acceptable salts thereof:

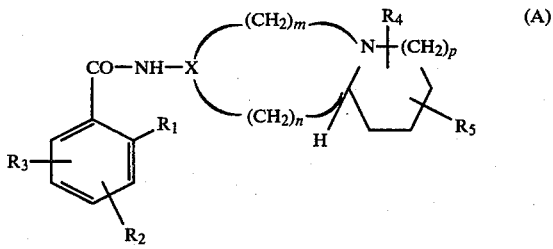

wherein:
$R_1$ is a $C_{1-6}$ alkoxy group;
$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acyl amino, aminocarbonyl or aminosulphone optionally substituted by one or two $C_{1-6}$ alkyl groups, $C_{1-6}$ alkylsulphone or nitro groups;
X is either a nitrogen atom, in which case m+n is 3 to 5, m is 2 to 4 and n is 1 to 3; or X is CH in which case m+n is 2 to 5, m is 1 to 5, and n is 0 to 4;
p is 0 to 3; and
$R_4$ is hydrogen, $C_{1-6}$ alkyl, phenyl or phenyl-$C_{1-6}$ alkyl, either of which phenyl moiety may be substituted by $C_{1-6}$ alkyl, $C_{1-6}$ alkoxy, $CF_3$ or halogen, and $R_5$ is hydrogen; or $R_4$ and $R_5$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; as dopamine antagonists having use in the treatment of disorders of the gastro-intestinal function and/or in the treatment of emesis.

A novel class of compounds has now been discovered which is structurally distinct from the known compounds of the formula (I) but also has useful pharmacological activity, such as dopamine antagonist activity.

Accordingly the present invention provides a compound of the formula (I):

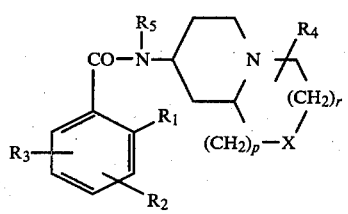

and pharmaceutically acceptable salts and N-oxides thereof, wherein:
$R_1$ is a $C_{1-6}$ alkoxy group;
$R_2$ and $R_3$ are the same or different and are hydrogen, halogen, $CF_3$, $C_{1-7}$ acyl, $C_{1-7}$ acylamino, $C_{1-6}$ alkyl-$S(O)_n$ wherein n is 0, 1 or 2, nitro, $C_{1-6}$ alkoxy, hydroxy, or amino, aminocarbonyl or aminosulphonyl optionally substituted by one or two $C_{1-6}$ alkyl groups;
or $R_1$ and $R_2$ taken together are methylenedioxy or ethylenedioxy in which case $R_3$ is any one of the groups given for $R_1$ and $R_2$ above;
$R_4$ is hydrogen, $C_{1-4}$ alkyl, phenyl or phenyl-$C_{1-4}$ alkyl;
$R_5$ is hydrogen or $C_{1-4}$ alkyl;
X is an oxygen or sulphur atom; or a sulphoxide group >S~O;
p is 1 or 2; and
r is 1 or 2.

Within formula (I) there is a group of compounds wherein $R_1$, $R_5$, X, p and r as defined, $R_2$ and $R_3$ are the same or different and are hydrogen, halogen, $CF_3$, $C_{1-7}$ acyl, $C_{1-7}$ acylamino, $C_{1-6}$ alkyl-$S(O)_n$ wherein n is 0, 1 or 2, nitro, or amino, aminocarbonyl or aminosulphonyl optionally substituted by one or two $C_{1-6}$ alkyl groups; and $R_4$ is hydrogen, $C_{1-4}$ alkyl or phenyl and substitutes the carbon atom in the X ring adjacent the nitrogen.

Within the group of compounds defined in the preceding paragraph there is a further group of compounds wherein the variables $R_1$, $R_4$, $R_5$, p and r are as defined, $R_2$ and $R_3$ are as defined except that when alkyl-$S(O)_n$, n must be 2 (ie alkylsulphonyl), and X may only be an oxygen or sulphur atom.

Suitable examples of the group $R_1$ include methoxy, ethoxy and n- and iso-propoxy. Preferably $R_1$ is a methoxy group.

Suitable examples of $R_2$ and $R_3$ include the following atoms and groups: hydrogen; chlorine, bromine; $CF_3$; formyl, acetyl, propionyl, n- and iso-butyryl; formylamino, acetylamino, propionylamino, n- and iso-butyrylamino; methyl, ethyl and n- and iso-propylsulphone, -sulphinyl or -thia; nitro; methoxy, ethoxy and n- and iso-propoxy; hydroxy; amino, aminocarbonyl and aminosulphonyl and amino, aminocarbonyl, and aminosulphonyl substituted by one or two methyl, ethyl, n- or iso-propyl groups.

When $R_1$ and $R_2$ taken together are methylenedioxy or ethylenedioxy, they are most suitably ethylenedioxy.

Particularly suitable $R_2$ and $R_3$ groups include hydrogen, halogen and amino; and as "intermediates", acyl-amino and nitro, which can conveniently be converted to the corresponding amino groups.

It is generally preferred that $R_2$ is in the 4-position relative to the carbonyl side chain, for greater activity in the resultant compound of the formula (I). For the same reason, it is generally preferred that $R_3$ is in the 5-position relative to the carbonyl side chain.

Particularly preferred $R_2$ groups include 4-amino and 4-acylamino. Most preferably $R_2$ is 4-amino. Particularly preferred $R_3$ groups include 5-halo, such as 5-chloro.

In other useful compounds $R_2$ is hydrogen, 4-halo (eg chloro), or amino; and $R_3$ is 5-$C_{1-6}$ alkyl $S(O)_n$ (such as 5-methylsulphonyl, -sulphinyl or -thia) or 5-optionally alkylated aminosulphonyl.

$R_4$ may substitute any carbon in the X ring (apart from the bridgehead carbon), but preferably substitutes the carbon atom adjacent the nitrogen atom.

Suitable examples of $R_4$ include hydrogen, methyl, ethyl, n- and iso-propyl, phenyl and benzyl. Phenyl groups in $R_4$ may be substituted by one or more $C_{1-4}$ alkoxy (such as ethoxy), $C_{1-4}$ alkyl (such as methyl), fluoro, chloro or $CF_3$. Often $R_4$ will be hydrogen, $C_{1-4}$ alkyl or phenyl. Most suitably $R_4$ is hydrogen or methyl.

Suitable examples of $R_5$ include hydrogen, methyl, ethyl and n- and iso-propyl. More suitably $R_5$ is hydrogen or methyl, preferably hydrogen.

Generally X is most suitably oxygen.

(The X is >S~O group has been referred to above as the sulphoxide group. The skilled chemist will appreciate that in naming a compound containing such a >S~O group, the group can be referred to as "oxothia", and indeed this terminology has been used in Example 15.)

Preferably p is 1.
Preferably r is 1.

It is generally preferred for higher activity that the bond between the benzamide moiety and the cyclic side chain (i.e. between the $R_5$ substituted nitrogen atom and the ring carbon atom to which this nitrogen atom is joined) in the compounds of formula (I) is axial (When used herein in relation to this bond axial is assigned with the bicyclic drawn with a trans ring fusion, and is also referred to as α. Equatorial is similarly assigned, and is also referred to as β.)

The pharmaceutically acceptable salts of the compound of the formula (I) include acid addition salts with conventional acids such as hydrochloric, hydrobromic, phosphoric, sulphuric, citric, tartaric, lactic and acetic acid and the like.

The pharmaceutically acceptable salts of the compounds of the formula (I) also include quaternary ammonium salts. Examples of such salts include salts with compounds such as $R_6$-Y wherein $R_6$ is $C_{1-6}$ alkyl, phenyl-$C_{1-6}$ alkyl or $C_{5-7}$ cycloalkyl, and Y is an anion of an acid. Suitable examples of $R_6$ include methyl, ethyl and n- and iso-propyl; and benzyl and phenyl ethyl. Suitable examples of Y include the halides such as chloride, bromine and iodide.

From the aforesaid it will be seen that suitably the moiety of formula (II):

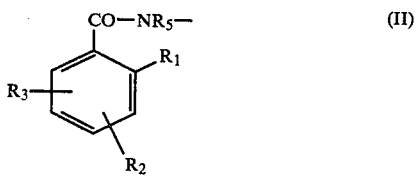

in a compound of the formula (I) will have the structure (III):

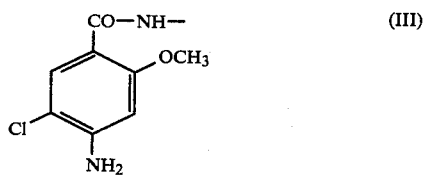

From the aforesaid it will also be appreciated that preferably the moiety of formula (IV):

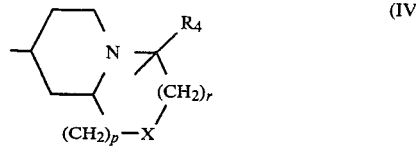

in the compound of formula (I) is of the formula (V):

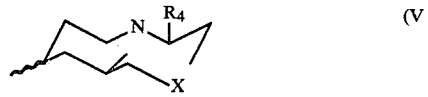

Thus a preferred sub-group of compounds within formula (I) is of formula (VI):

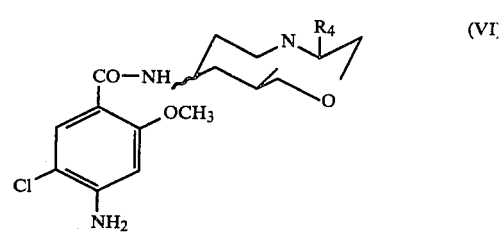

In formula (VI), suitably the bond indicated is axial.

Also in formula (VI) suitably $R_4$ is hydrogen or methyl.

Another preferred sub-group of compounds within formula (I) is of formula (VII):

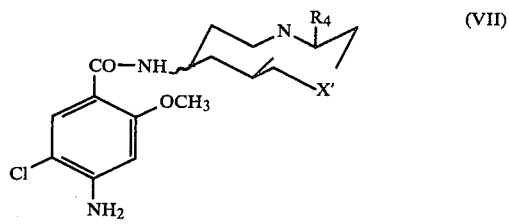

wherein X' is S or S~O, preferably S.

In formula (VII), suitably the bond indicated is axial.

Also in formula (VII) suitably $R_4$ is hydrogen or methyl.

It will of course be realised that the compounds of the formula (I) have chiral centres, and thus are capable of existing in a number of stereoisomeric forms. The invention extends to each of these stereoisomeric forms, and to mixtures thereof (including racemates). The different steroisomeric forms may be separated one from the other by the usual methods, or any given isomer may be obtained by stereospecific or asymmetric synthesis.

The invention also provides a process for the preparation of a compound of the formula (I), which process comprises reacting an acid of the formula (VIII):

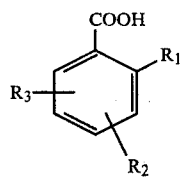

(VIII)

or a reactive derivative thereof, with a compound of the formula (IX):

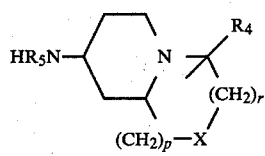

(IX)

wherein the variable groups are as defined in formula (I); and thereafter if desired or necessary converting a group $R_2$, $R_3$ or X in the thus formed compound to another group $R_2$, $R_3$ or X respectively.

"Reactive derivative" when used herein means a derivative of the compound (VIII) which can be reacted with the compound (IX) to form an amido linkage between the acid group of the compound (VIII) and the amino group of the compound of the formula (IX).

Often this reactive derivative will be the acid halide, such as the acid chloride, of the acid (VIII). In such cases the reaction will normally be carried out in an inert solvent, preferably in the presence of an acid acceptor. The inert solvent can be any solvent inert to both reactants, such as benzene, toluene, diethyl ether or the like. The acid acceptor is suitably an organic base such as a tertiary amine, e.g. triethylamine, trimethylamine, pyridine or picoline, or an inorganic acid acceptor, such as calcium carbonate, sodium carbonate, potassium carbonate or the like. It should be noted also that it is possible to use certain acid acceptors as the inert solvent, for example organic bases.

Another useful reactive derivative of the acid (VIII) that may be used is an ester, such as a methyl, ethyl, propyl or butyl ester, in which case the reaction is normally carried out by heating the reactants together in an inert solvent such as ethylene glycol.

The reaction may also be carried out by forming an anhydride of the acid (VIII) in the usual manner, and reacting that with the compound (IX); normally a conventional mixed anhydride will be used; or by reacting the acid (VIII) and the compound (IX) in the presence of a dehydrating catalyst such as a carbodiimide, for example dicyclohexylcarbodiimide.

It will be realised that in the compound of the formula (I) the linkage between the —NR$_5$— moiety and the cyclic side chain may have an $\alpha$ or $\beta$ orientation with respect to the ring of the bicyclic moiety to which it is attached. A mixture of $\alpha$ and $\beta$ isomers of the compound of the formula (I) may be synthesised non-stereospecifically and the desired isomer separated conventionally therefrom, e.g. by chromatography; or alternatively the $\alpha$ or $\beta$ isomer may if desired be synthesised from the corresponding $\alpha$ or $\beta$ form of the compound of the formula (IX).

Alternatively, a mixture of the $\alpha$ and $\beta$ isomers of the compound of the formula (IX) may be synthesised non-stereospecifically and the desired isomer separated conventionally therefrom, e.g. by chromatography. However, in this case it is generally more convenient to react the mixture to give a mixture of $\alpha$ and $\beta$ isomers of the compound of the formula (I) and to separate these if desired as hereinbefore described.

The intermediates of formula (IX) may be prepared by a process which depends on whether the $\alpha$ or $\beta$ forms is desired, or a mixture thereof.

To prepare $\alpha$ or axial compounds of formula (IX), a compound of formula (X) is reduced:

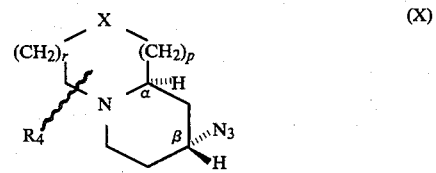

(X)

This reduction is conveniently carried out with lithium aluminium hydride under the usual conditions.

Compounds of formula (X) may themselves be prepared by reaction of a compound of the formula (XI):

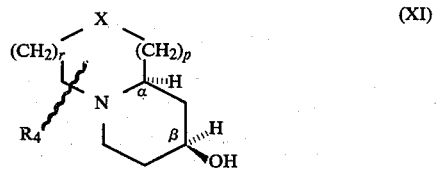

(XI)

to effect conversion of hydroxy to azido, with inversion of stereochemistry.

This reaction may be carried out in the general manner described in A. K. Bose et. al., Tetrahedron Letters 1977, 23, 1977). For example, the reaction may be effected with triphenylphosphine, diethyl azodicarboxylate and diphenylphosphoryl azide.

Compounds of the formula (XI) are important intermediates, as from these compounds the $\beta$ form of compounds of the formula (IX), and $\alpha/\beta$ mixtures thereof, may be prepared.

For example, reaction of a compound of formula (XI) with a base and fluorenone yields a compound of formula (XII):

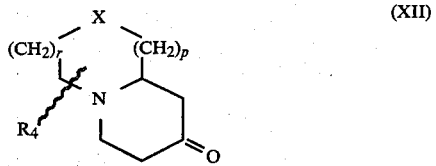

(XII)

The compounds of formula (XII) may be converted to compounds of formula (XIII):

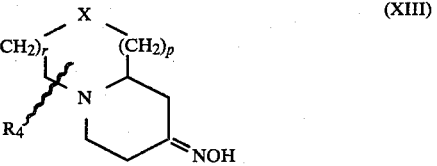

(XIII)

with hydroxylamine. We have found that this reaction is suitably carried out with pyridine and hydroxylamine hydrochloride at reflux temperatures.

Reduction of a compound of formula (XIII) with lithium aluminium hydride gives a mixture of axial (α) and equatorial (β) amines of formula (IX) where R₅ is H.

In contrast, a dissolving metal reduction of a compound of formula (XIII) is substantially stereospecific and yields mainly the β amines of formula (IX) (any minor proportions of the undesired isomer prepared in this process can be separated in conventional manner). Such reductions may suitably be carried out with sodium and amyl alcohol.

Returning now to compounds of the formula (XI), these compounds may be prepared from a compound of formula (XIV):

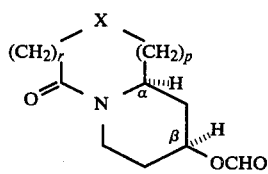
(XIV)

by a process which depends on the nature of R₄.

When R₄ is hydrogen, the reaction may be carried out by reduction with for example lithium aluminium hydride.

When R₄ is $C_{1-4}$ alkyl or phenyl, and substitutes the carbon adjacent the nitrogen, the compound of formula (XIV) is converted with first base, such as sodium hydroxide, and second a silylating agent, such as $(CH_3)_3SiCl$ or hexamethyldisilazane, to the silyl ether of formula (XV):

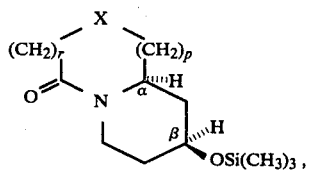
(XV)

which in turn is converted to the desired compound of formula (XI) with a R₄ metal complex, such as R₄Li, and subsequent reduction, for example with sodium borohydride.

The intermediates of formula (XIV) may themselves be prepared by treating a compound of formula (XVI):

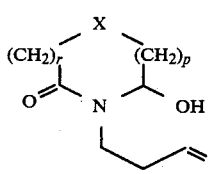
(XVI)

with formic acid.

Compounds of formula (XVI) may be prepared by reduction, for example with sodium borohydride and hydrogen chloride, of a compound of formula (XVII):

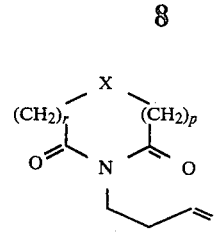
(XVII), which compounds of formula (XVII) may themselves be prepared by reaction of a compound of formula (XVIII):

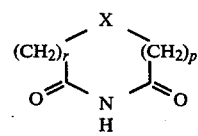
(XVIII)

with an alkylene halide, such as 4-brombut-1-ene, using base.

To obtain a compound of the formula (XI) wherein R₄ is $C_{1-4}$ alkyl, phenyl or phenyl $C_{1-4}$ alkyl and substitutes the X ring at the carbon other than the carbon adjacent the nitrogen, a compound of formula (XIV)' is reduced, for example with lithium aluminium hydride:

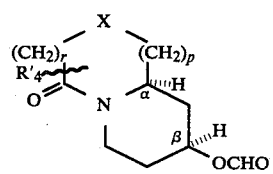
(XIV)'

(wherein R₄' is $C_{1-4}$ alkyl or phenyl).

Such compounds of the formula (XIV)' may be prepared by the (XVIII)→(XVII) to (XVI)→(XIV) route as described for compounds of formula (XIV), except that the R₄' substituent is present in each of the compounds (XVIII), (XVII) and (XVI) to correspond to the R₄ in compounds (XIV)'. (It will of course be appreciated that in such a reaction sequence the (XVII) to (XVI) reduction will give a mixture of isomers which can be separated by conventional means.)

The aforesaid processes of course yield a compound of the formula (IX) wherein R₅ is hydrogen.

If a compound of formula (IX) wherein R₅ is alkyl is desired, it may simply be prepared from the corresponding R₅ is hydrogen compond by alkylation. This may be effected in any suitable manner, for example by acylation with an anhydride followed by reduction with lithium aluminium hydride.

It will be appreciated that any enantiomer, or mixture of enantiomers, of the compounds of formulae (X), (XI), (XIV) and (XV) may be used provided it has the depicted spatial relationship between carbons a and b.

The intermediates of the formula (VIII) are known compounds, or may be prepared in analogous manner.

The N-oxides of the compounds of formula (I) may be prepared in conventional manner, for example by treatment with a per-acid, such as m-chloroperbenzoic acid.

The acid addition salts of compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_6Y$ as defined. This reaction is suitably carried out in an appropriate solvent such as acetone, methanol, ethanol, dimethylformamide and the like, at ambient or raised temperature and pressure.

The interconversion of suitable groups $R_2$ and $R_3$ after formation of a compound of the formula (I) or corresponding intermediate therefor may be carried out by conventional methods. By way of example nitro groups may be reduced to amino groups in the normal manner, and acylamino groups may be converted to amino groups also by conventional methods. Also a compound of the formula (I) wherein $R_2$ or $R_3$ is halogen can be prepared by a conventional halogenation of the corresponding compound of the formula (I) wherein the said $R_2$ or $R_3$ is hydrogen. Further, compounds wherein $R_2$ or $R_3$ are $C_{1-6}$ alkylsulphonyl may be prepared by oxidation of the corresponding $C_{1-6}$ alkyl sulphinyl compounds; and such $C_{1-6}$ alkylsulphinyl compounds may be prepared by oxidation of the corresponding $C_{1-6}$ alkylthia compound*. In regard to X, when X is S the compounds may be oxidised to $S \sim O$ compounds, suitably with sodium periodate. Accordingly it will be realised that compounds of the formula (I) containing a $R_2$, $R_3$ or X group which is convertible to another $R_2$, $R_3$ or X group are useful intermediates, and as such form an important aspect of the invention.
*(it will be appreciated that when X is S it may be preferable to have carried out this step on the acid (VIII) prior to coupling)

As hereinbefore stated, the compounds of the formula (I) are dopamine antagonists.

The compounds of the formula (I) may be used in the treatment of disorders related to impaired gastro-intestinal motility, such as retarded gastric emptying, dyspepsia, flatulence, oesophagal reflux, peptic ulcer and emesis.

The invention therefore also provides a pharmaceutical composition comprising a compound of the formula (I), or a pharmaceutically acceptable salt thereof, together with a pharmaceutically acceptable carrier.

Such compositions may be adapted for oral or parenteral administration, and as such may be in the form of tablets, capsules, oral liquid preparations, powders, granules, lozenges, reconstitutable powders, injectable and infusable solutions or suspensions and the like; the compositions may also be in the form of suppositories and the like. Normally, orally administrable compositions are preferred.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented in a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention further provides a method of treatment of maladies in humans comprising the administration of an effective amount of a compound of the formula (I) or a pharmaceutically acceptable salt thereof. The "effective amount" will depend in the usual way on a number of factors such as the nature and severity of the malady to be treated, the weight of the sufferer, and the actual compound used.

However by way of illustration, unit doses will suitably contain 0.1 to 20 mgs of the compound of formula (I), for example 0.5 to 10 mgs.

Again by way of illustration, such unit doses will suitably be administered more than once a day, for example 2, 3, 4, 5 or 6 times a day, in such a way that the total daily dose is suitably in the range 0.01 to 10 mg/kg per day.

Compounds of the formula (I) have the ability to potentiate the effect of conventional analgesics in migraine treatment when administered concurrently with the analgesic.

Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The following Examples illustrate the preparation of the compounds of formula (I) and the following Descriptions illustrate the preparation of intermediates thereto.

In the Examples, ($\pm$) of course indicates that the compound is a racemate. However, for the sake of convenience, the structural formula of only one enantiomer has been shown.

Description 1

(a) 1-(4-But-1-enyl)morpholine-2,6-dione (D.1)

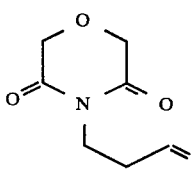

To a stirred solution of morpholine-2,6-dione (11.6 g) in dry DMF (100 ml) was added 80% sodium hydride (3.4 g). On cessation of the gas evolution (ca. ½ hour), 4-bromobut-1-ene (13.6 g) was added and the whole refluxed for 2 hours. On cooling, the reaction mixture was poured into ice/water (300 ml) and extracted with ether (3×200 ml) and ethyl acetate (200 ml).

Fractional distillation afforded the 1-(4-but-1-enyl)-morpholine-2,6-dione (D.1) (10.0 g, 60%).

b.p. 84°-8°/0.1 mm.

n.m.r. (δ, CDCl$_3$): 6.05-5.35 (m, 1H, H$_2$C=C$\underline{H}$—CH$_2$); 5.2-4.75 (m, 2H, $\underline{H_2}$C=CH—); 4.25 (s, 4H, O(C$\underline{H_2}$CO)$_2$N—); 3.73 (t, 2H, >N—C$\underline{H}$$_2$—CH$_2$—; J=7 Hz); 2.5-2 (m, 2H, —CH$_2$—C$\underline{H}$$_2$—CH=).

(b) (±) 1-aza-8β-Formyloxy-6α-H-4-oxabicyclo[4,4,0]decane-2-one (D.2)

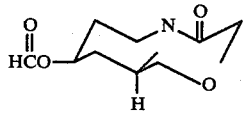

The 1-(4-but-1-enyl)morpholine-2,6-dione (D.1) (5 g) was reduced with sodium borohydride (10.8 g) in absolute ethanol (300 ml) at −15° C. for 5 hours, during which time 3-5 drops of ethanolic hydrogen chloride (4.5 N) was added at 15 minute intervals.

The excess sodium borohydride was destroyed with excess ethanolic hydrogen chloride (to pH 3) and the ethanol removed by rotary evaporation. Addition of saturated aqueous sodium bicarbonate solution and extraction with methylene chloride gave the crude 1-(4-but-1-enyl)-2-hydroxymorpholine-6-one (6.0 g).

The crude 1-(4-but-1-enyl)-2-hydroxymorpholine-6-one was dissolved in 98% formic acid and the solution stored overnight at ambient temperatures. The formic acid was removed by rotary evaporation and the residue taken up in methylene chloride, washed with aqueous sodium bicarbonate solution and dried (MgSO$_4$). Removal of the solvent gave the crude (±) 1-aza-8-formyloxy-6α-H-4-oxa bicyclo[4,4,0]decane-2-one (D.2) (5.6 g, ca. 100%).

n.m.r. (δ, CDCl$_3$): 7.98 (s, 1H, O$_2$C$\underline{H}$); 5.7-3.2 (m, 7H including 4.1; s, 2H, —OCH$_2$$\overset{O}{\underset{\|}{C}}$—);

3.0-1.0 (m, 5H, remaining protons).

(c) (±) 1-aza-8β-Hydroxy-6α-H-4-oxabicyclo[4,4,0]decane (D.3) intermediate for Compounds 1 and 2

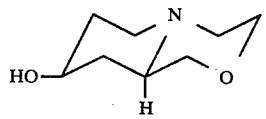

The crude (±) 1-aza-8β-formyloxy-6α-H-4-oxabicyclo[4,4,0]decane-2-one (D.2) (2.8 g) was reduced with lithium aluminium hydride (0.8 g) in ether. Hydrolysis, filtration and distillation afforded the (±) 1-aza-8β-hydroxy-6α-H-4-oxabicyclo[4,4,0]decane (D.3) (1.5 g, 65% from D.1).

b.p. 85°-96°/0.1 mm.

n.m.r. (δ, CDCl$_3$): 4.2-0.9 (m, 15H, all protons).

(d) (±) 1-aza-8α-Azido-6α-H-4-oxabicyclo[4,4,0]decane (D.4) intermediate for Compounds 1 and 2

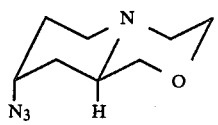

To a dry, stirred THF (30 ml) solution of triphenylphosphine (2.75 g) and diethyl azodicarboxylate (1.9 g) at 0° C. was added (±) 1-aza-8β-hydroxy-6α-H-4-oxabicyclo[4,4,0]decane (D.3) (1.5 g). After stirring for 10 mins diphenylphosphoryl azide (2.9 g) in dry THF (10 ml) was added during 10 mins and the mixture stirred at ambient temperature for 3 days.

The THF was removed and replaced by methylene chloride. The product was extracted into 5 N hydrochloric acid (10 ml) and washed with methylene chloride (3×50 ml). Basification and saturation with potassium carbonate, re-extraction with methylene chloride and removal of the solvent gave the crude (±) 1-aza-8α-azido-6α-H-4-oxabicyclo[4,4,0]decane (D.4) (1.6 g, 90%).

i.r. (film) ν$_{(N3)}$: 2090 cm$^{-1}$.

(e) (±) 8α-Amino-1-aza-6α-H-4-oxabicyclo[4,4,0]-decane (D.5) intermediate for Compounds 1 and 2

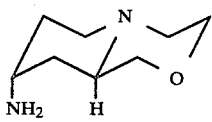

The crude (±) 1-aza-8α-azido-6α-H-4-oxabicyclo[4,4,0]decane (D.4) (1.6 g) was reduced with lithium aluminium hydride (0.3 g) in ether for 4 hours. Hydrolysis, extraction with methylene chloride and solvent removal afforded the crude (±) 8α-amino-1-aza-6α-H-4-oxabicyclo[4,4,0]decane (D.5) (1.5 g, ca. 100%).

Description 2

(a) (±) 1-Aza-6α-H-4-oxabicyclo[4,4,0]decane-8-one (D.6) intermediate for Compounds 3 and 4

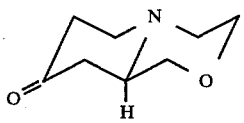

To a stirred solution of (±) 1-aza-8α-hydroxy-6α-H-4-oxabicyclo[4,4,0]decane (D.3) (2.8 g) and fluorenone (17 g) in dry benzene (70 ml) was added potassium tert. butoxide (5.6 g) and the solution stirred at room temperature for 30 mins. The product was extracted into 5 N hydrochloric acid (25 ml), and washed with methylene chloride (50 ml). The aqueous phase was neutralised then saturated with potassium carbonate and extracted with methylene chloride (3×100 ml). Removal of the solvent gave the crude (±) 1-aza-6α-H-4-oxabicyclo[4,4,0]decane-8-one (D.6) (3.0 g, ca 100%).

(b) (±) 1-Aza-6α-H-4-oxabicyclo[4,4,0]decane-8-one oxime (D.7) intermediate for Compounds 3 and 4

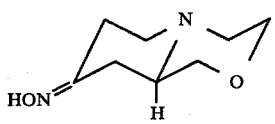

An ethanolic (30 ml) solution of (±) 1-aza-6α-H-4-oxabicyclo[4,4,0]decane-8-one (D.6) (3.0 g) was treated with pyridine (3 ml) and hydroxylamine hydrochloride (3 gm) and the mixture heated under reflux for 30 mins. On cooling, the ethanol was removed by rotary evaporation and the residue treated with dilute potassium carbonate solution. The product was extracted with methylene chloride and dried (K₂CO₃). Removal of the solvent afforded the crude (±) 1-aza-6α-H-4-oxabicyclo[4,4,0]decane-8-one oxime (D.7) (3.0 g, ca 95%).

(c) (±) 8β-Amino-1-aza-6α-H-4-oxabicyclo[4,4,0]decane (D.8) intermediate for Compounds 3 and 4

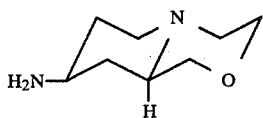

To a refluxing amyl alcohol (100 ml) solution of the crude (±) 1-aza-6α-H-4-oxabicyclo[4,4,0]decane-8-one oxime (D.7) (3.0 g) was added sodium (ca 3.0 g) portionwise over 1 hour. The cooled reaction mixture was then treated with 5 N hydrochloric acid (ca 80 ml) and extracted with ethyl acetate. The acidic aqueous layer was separated, neutralised and saturated with potassium carbonate and re-extracted with methylene chloride (4×150 ml). Distillation of the organic extracts gave the (±) 8β-amino-1-aza-6α-H-4-oxabicyclo[4,4,0]decane (D.8) (1.5 g, 50%).
b.p. 58°-62°/0.1 mm.

Description 3

(a) (±) 1-Aza-8β-hydroxy-6α-H-4-oxabicyclo[4,4,0]decan-2-one (D.9) intermediate for Compounds 5 and 6

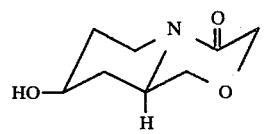

To an ethanolic solution (50 ml) of (±) 1-aza-8β-formyloxy-6α-H-4-oxabicyclo[4,4,0]-decane-2-one (D.2) (7.0 g) was added aqueous 2.5 N sodium hydroxide solution (14 ml) and the mixture stood for 10 mins. at room temperature. The ethanol was removed by rotary evaporation and the residue extracted with methylene chloride. Distillation of the organic extracts afforded the (±) 1-aza-8β-hydroxy-6α-H-4-oxabicyclo[4,4,0]-decane-2-one (D.9) (4.1 g, 68%).
b.p. 80°-90°/0.1 mm.

(b) (±) 1-Aza-8β-hydroxy-2β-methyl-6α-H-4-oxabicyclo[4,4,0]decane (D.10) intermediate for Compounds 5 and 6

An immiscible mixture of (±) 1-aza-8β-hydroxy-6α-H-4-oxabicyclo[4,4,0]decane-2-one (D.9) (2.3 g) and hexamethyldisilazane (4 ml) was treated with 2 drops of conc. sulphuric acid and subsequently heated to 80° until a single phase was obtained (ca. ½ hour). On cooling, petroleum ether (40°-60°) (200 ml) was added and the solution washed with aqueous sodium bicarbonate (20 ml) and dried (MgSO₄). Filtration and removal of the petroleum ether gave the crude trimethyl silyl ether (3.0 g).

To a cooled (−30°) stirred solution of the trimethyl silyl ether in dry ether (50 ml) was added a 0.6 M solution of methyl lithium (40 ml) with subsequent stirring at room temperature for 2 hours. Saturated sodium bicarbonate solution (20 ml) was added, the aqueous layer separated and extracted with methylene chloride (3×50 ml). The combined organic extracts were dried (K₂CO₃), filtered and concentrated.

Ice-cold ethanol (50 ml) was added followed by 4.5 M ethanolic hydrogen chloride (5 ml) and subsequently stirred at 0° C. with sodium borohydride (3.0 g) for 2 hours.

The ethanol was removed by rotary evaporation and the residue extracted with methylene chloride (3×100 ml). Distillation of the organic extracts gave the (±) 1-aza-8β-hydroxy-2β-methyl-6α-H-4-oxabicyclo[4,4,0]-decane (D.10) (1.2 g, 55%)
b.p. 96°/0.1 mm.
n.m.r. (δ, CCl₄): 4.2-0.87 (m, 17H, includes 0.92, d, 3H, >CHC$\underline{H}_3$ J=6 Hz).

(c) (±)
1-Aza-8α-azido-2β-methyl-6α-H-4-oxabicyclo[4,4,0]-decane (D.11) intermediate for Compounds 5 and 6

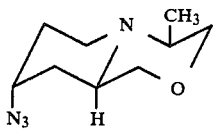
(D.11)

Following the procedures outlined in Description 1, the (±) 1-aza-8β-hydroxy-2β-methyl-6α-H-4-oxabicyclo[4,4,0]decane (D.10) (1.2 g) was converted to (±)-1-aza-8α-azido-2β-methyl-6α-H-4-oxabicyclo[4,4,0]decane (D.11). (1.05 g, 75%).
i.r. (film) $\nu_{(N_3)}$: 2090 cm$^{-1}$.

(d) (±)
8α-Amino-1-aza-2β-methyl-6α-H-4-oxabicyclo[4,4,0]-decane (D.12) intermediate for Compounds 5 and 6

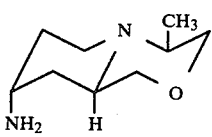
(D.12)

Following the procedures outlined in Description 1, the (±) 1-aza-8α-azido-2β-methyl-6α-H-4-oxabicyclo[4,4,0]decane (D.11) (1.05 g) was converted to (±) 8α-amino-1-aza-2β-methyl-6α-H-4-oxabicyclo[4,4,0]-decane (D.12) (0.9 g, 100%).

Description 4

(a) 1-(4-But-1-enyl)thiomorpholine-2,6-dione (D.13)

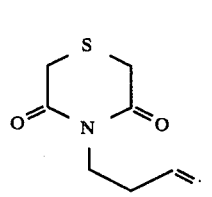
(D.13)

Following the procedures outlined in Description 1, the thiomorpholine-2,6-dione (18.8 g) was converted into 1-(4-but-1-enyl)thiomorpholine-2,6-dione (D.13)
b.p. 106°/0.4 mm (16 g, 60%).
n.m.r. (δ, CDCl$_3$): 6.1–5.35 (m, 1H, H$_2$C=C$\underline{H}$—CH$_2$—); 5.2–4.75 (m, 2H, $\underline{H_2}$C=CH—); 3.83 (t, 2$\underline{H}$, J 7 Hz, >NC$\underline{H_2}$—); 3.48 (s, 4H, S(C$\underline{H_2}$CO)$_2$N—); 2.5–2 (m, 2H, —CH$_2$—C$\underline{H_2}$CH=).

(b) (±)
1-Aza-8β-formyloxy-6α-H-4-thiabicyclo[4,4,0]decane-2-one (D.14)

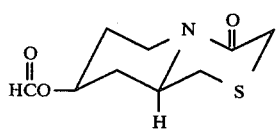
(D.14)

Following the procedures outlined in Description 1, the 1-(4-but-1-enyl)thiomorpholine-2,6-dione (D.13) (7.2 g) was converted into crude (±)1-aza-8β-formyloxy-6α-H-4-thiabicyclo[4,4,0]decane-2-one (D.14) (6.6 g, 79%).

n.m.r. (δ, CDCl$_3$): 7.98 (s, 1H, OOC$\underline{H}$); 5.7–1.2 (m, 12H including 3.3, s, 2H,

(c) (±)
1-Aza-8β-hydroxy-6α-H-4-thiabicyclo[4,4,0]decane (D.15)

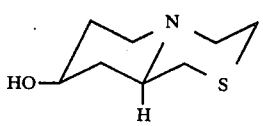
(D.15)

Following the procedures outlined in Description 1, the (±) 1-aza-8β-formyloxy-6α-H-4-thiabicyclo[4,4,0]-decane-2-one (D.14) (9 g) was converted into (±) 1-aza-8β-hydroxy-6α-H-4-thiabicyclo[4,4,0]decane (D.15) (5.8 g, 80%)
b.p. 120°/0.2 mm m.p. 130°-3°.

(d) (±)
1-Aza-8α,β-azido-6α-H-4-thiabicyclo[4,4,0]decane (D.16) intermediate for Compounds 7 and 8

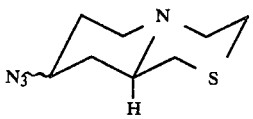

Following the procedures outline in Description 1, the (±) 1-aza-8β-hydroxy-6α-H-4-thiabicyclo[4,4,0]-decane (D.15) (2.5 g) was converted into a crude isomeric mixture of (±) 1-aza-8α-, and 1-aza-8β-azido-6α-H-4-thiabicyclo[4,4,0]decane (D. 16) (2.8 g, 95%)
i.r. (film) $\nu_{(N_3)}$: 2090 cm$^{-1}$.

(e) (±)
8α,βAmino-1-aza-6α-H-4-thiabicyclo[4,4,0]decane (D.17) intermediate for Compounds 7 and 8

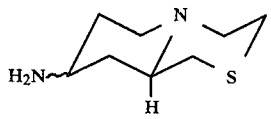
(D.17)

Following the procedures outlined in Description 1, the (±) 1-aza-8α,β-azido-6α-H-4-thiabicyclo[4,4,0]decane (D.16) was converted into a crude isomeric mixture of (±) 8α,β-amino-1-aza-6α-H-4-thiabicyclo[4,4,0]decane (D.17) (2.4 g, ca 100%).

Description 5

(a) (±) 1-Aza-6α-H-4-thiabicyclo[4,4,0]decane-8-one (D.18) intermediate for Compounds 9, 10, 19, 20 and 21

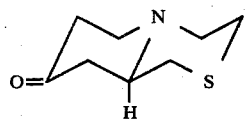

Following the procedures outline in Description 2, the (±) 1-aza-8β-hydroxy-6α-H-4-thiabicyclo[4,4,0]-decane (D.15) (prepared as in Description 15) (3.1 g) was converted into (±) 1-aza-6α-H-4-thiabicyclo[4,4,0]decane-8-one (D.18) (2.6 g, 80%).

(b) (±) 1-Aza-6α-H-4-thiabicyclo[4,4,0]decane-8-one oxime (D.19) intermediate for Compound 9, 10, 19, 20 and 21

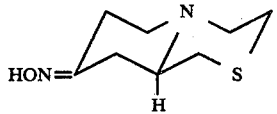

Following the procedures outlined in Description 2, the (±) 1-aza-6α-H-4-thiabicyclo[4,4,0]decane-8-one (D.18) 2.6 g) was converted into the crude (±) 1-aza-6α-H-4-thiabicyclo[4,4,0]decane-8-one oxime (D.19) (2.8 g, ca 100%), used without purification.

(c) (±) 8β-Amino-1-aza-6α-H-4-thiabicyclo[4,4,0]decane (D.20) intermediate for Compounds 9, 10, 19, 20 and 21

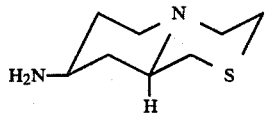

Following the procedures in Description 2, the (±) 1-aza-6α-H-4-thiabicyclo[4,4,0]decan-8-one oxime (D.19) (2.8 g) was converted into the crude (±) 8β-amino-1-aza-6α-H-4-thiabicyclo[4,4,0]decane (D.20) (2.5 g, ca 100%).

Description 6

(a) (±) 1-Aza-8β-Hydroxy-2β-phenyl-6α-H-4-oxabicyclo[4,4,0]decane (D.21) intermediate for Compounds 11, 12, 13 and 14

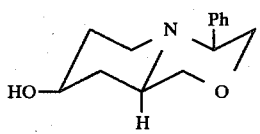

To a cooled (0° C.) stirred solution of bromobenzene (6.2 g) in dry ether (50 ml) was added a 1.6 M solution of n-butyl lithium in hexane (25 ml) and the solution was stirred at 0° C. for 30 minutes. On further cooling to −30° C., a solution of (±) 1-aza-8β-trimethylsiloxy-6α-H-4-oxabicyclo[4,4,0]decane-2-one (4.3 g crude) (see Description 3(b)) in dry ether (25 ml) was added over 5 minutes and the resulting solution stirred to room temperature over 2 hours, during which time a white precipitate formed. The stirred suspension was then cooled to 0° C. and 25 ml of a saturated aqueous potassium carbonate solution (25 ml), followed by methylene chloride (100 ml) was added and the organic upper layer separated, dried ($K_2CO_3$), filtered and concentrated in vacuo.

Ice-cold ethanol (100 ml) was then added followed by 5 N ethanolic hydrogen chloride (3.6 ml) and subsequently stirred at 0° C. with sodium borohydride (4 g) for 2 hours.

The ethanol was removed by rotary evaporation and the residue extracted with methylene chloride (3×100 ml). Column chromatography (silica, ether eluent) gave the (±) 1-aza-8β-hydroxy-2β-phenyl-6α-H-4-oxabicyclo[4,4,0]decane (D.21) as an oil (1.6 g, 24%).

(b) (±) 1-Aza-8α-azido-2β-phenyl-6α-H-4-oxabicyclo[4,4,0]-decane (D.22) intermediate for Compounds 11 and 12

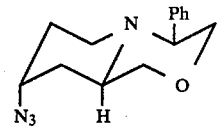

Following the procedures outlined in Description 1, the (±) 1-aza-8β-hydroxy-2β-phenyl-6α-H-oxabicyclo[4,4,0]decane (D.21) (1.6 g) was converted to (±) -1-aza-8α-azido-2β-phenyl-6α-H-4-oxabicyclo[4,4,0]-decane (D. 22) (1.4 g, 75%).

I.r. (film) $\nu_{(N_3)}$: 2090 cm$^{-1}$.

N.m.r. (δ, $CCl_4$): 7.6–7.0 (m, 5H, aromatic C-H). 4.2–1.1 (m, 13H, remaining C-H).

(c) (±) 8α-Amino-1-aza-2β-phenyl-6α-H-4-oxabicyclo[4,4,0]-decane (D.23) intermediate for Compounds 11 and 12

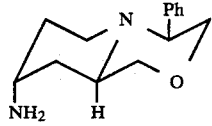

Following the procedures outlined in Description 1, the (±) 1-aza-8α-azido-2β-phenyl-6α-H-4-oxabicyclo[4,4,0]decane (D.22) (1.4 g) was converted to (±) 8α-amino-1-aza-2β-phenyl-6α-H-4-oxabicyclo[4,4,0]-decane (D.23) (1.3 g, 100%).

Description 7

(a) (±) 1-Aza-2β-phenyl-6α-H-4-oxabicyclo[4,4,0]decane-8-one (D.24) intermediate for Compounds 13 and 14

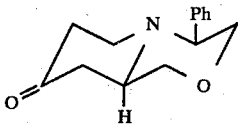

Following the procedures outlined in Description 2(a), the (±) 1-aza-8β-hydroxy-2β-phenyl-6α-H- oxabicyclo[4,4,0]decane (D.21) (2.6 g) was converted to (±) 1-aza-2β-phenyl-6α-H-4-oxabicyclo[4,4,0]decane-8-one (D.24) (2.4 g, 92%).

(b) (±) 1-Aza-2β-phenyl-6α-H-4-oxabicyclo[4,4,0]decane-8-one oxime (D.25) intermediate for Compounds 13 and 14

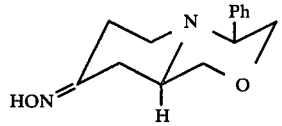

(D.25)

Following the procedures outlined in Description 2(b), the (±) 1-aza-2β-phenyl-6α-H-4-oxabicyclo[4,4,0]decane-8-one (D.24) (2.4 g) was converted to (±) 1-aza-2β-phenyl-6α-H-4-oxabicyclo[4,4,0]decane-8-one oxime (D.25) purified by column chromatography (silica, ether eluent) (2.3 g, 90%).

(c) (±) 8β-Amino-1-aza-2β-phenyl-6α-H-4-oxabicyclo[4,4,0]decane (D.26) intermediate for Compounds 13 and 14

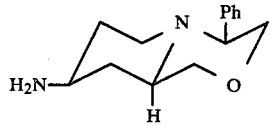

(D.26)

Following the procedures outlined in Description 2(c), the (±) 1-aza-2β-phenyl-6α-H-4-oxabicyclo[4,4,0]decane-8-one oxime (D.25) (2.3 g) was converted to (±) 8β-amino-1-aza-2β-phenyl-6α-H-4-oxabicyclo[4,4,0]decane (D.26) (2.1 g, 95%).

EXAMPLE 1

(±) 4-Acetamido-5-chloro-2-methoxy-N-(8α-1-aza-6α-H-4-oxabicyclo[4,4,0]decyl)benzamide (1)

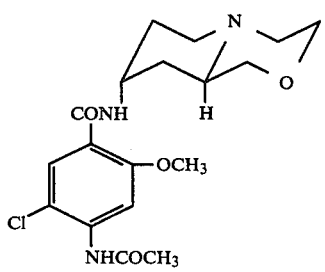

(1)

To 4-acetamido-5-chloro-2-methoxybenzoyl chloride (3.4 g) in toluene (150 ml) and triethylamine (3 ml) was added the crude (±) 8α-amino-1-aza-6α-H-4-oxabicyclo[4,4,0]decane (D.5) (1.5 g) in toluene (20 ml). The reaction mixture was stirred at room temperature for 4 hours, then treated with 2.5 N aqueous sodium hydroxide (10 ml). The toluene layer was separated, the aqueous layer extracted with chloroform (3×100 ml) and the combined organic extracts dried (K₂CO₃). The solvent was removed and chromatography of the product (neutral alumina, Brockman II, ethylacetate) gave the (±) 4-acetamido-5-chloro-2-methoxy-N-(8α-1-aza-6α-H-4-oxabicyclo[4,4,0]decyl)benzamide (1) m.p. 189°-92° (2.9 g, 80%).

n.m.r. (δ, CDCl₃): 8.27 (s, 1H, aryl H); 8.12 (s, 1H, aryl H); 8.2–7.2 (m, 2H, —CONH—CH<, CH₂CONH-Ar); 5.65–4.2 (m, 1H, 8β-H); 4.15–3 (m, 7H including 4.0 s, 3H, —OCH₃); 3–1.2 (m, 12H=CH₂ including 2.27, s, 3H, —COCH₃).

EXAMPLE 2

(±) 4-Amino-5-chloro-2-methoxy-N-(8α-1-aza-6α-H-4-oxabicyclo[4,4,0]decyl)benzamide (2)

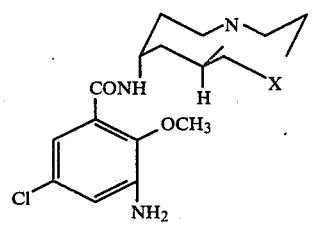

(2)

(1) (2.9 g) (prepared as in Example 1) was refluxed with an aqueous ethanol (water 5 ml, ethanol 50 ml) solution of potassium hydroxide (1 g) for 2 hours. The mixture was then cooled to room temperature and the ethanol removed by rotary evaporation. Trituration with water gave a white solid which was collected and recrystallised from ethylacetate yielding the (±) 4-amino-5-chloro-2-methoxy-N-(8α-1-aza-6α-H-4-oxabicyclo[4,4,0]decyl)benzamide (2) (1.35 g, 50%). m.p.=190°.

n.m.r (δ, CDCl₃): 8.3–7.8 (m, 1H, ArCONH—CH=); 8.03 (s, 1H, Acyl 6-H); 6.27 (s, 1H, Acyl 3-H); 4.7–1.3 (m, 19H, includes 3.9, s, 3H, —OCH₃).

EXAMPLE 3

(±) 4-Acetamido-5-chloro-2-methoxy-N-(8β-1aza-6α-H-4-oxabicyclo[4,4,0]decyl)benzamide (3)

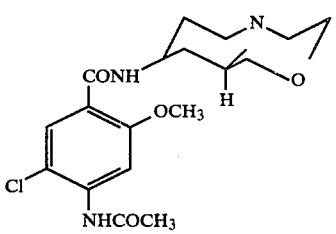

(3)

Following the procedures outlined in Example 1, the (±) 8β-amino-1-aza-6α-H-4-oxabicyclo[4,4,0]decane (D.8) (1.5 g) was converted to (±) 4-acetamido-5-chloro-2-methoxy-N-(8β-1-aza-6α-H-4-oxabicyclo[4,4,0]decyl)benzamide (3) (2.6 g, 70%) m.p. 188°–9°.

n.m.r (δ, CDCl₃): 8.18 (s, 1H, aryl-H); 8.05 (s, 1H, aryl-H); 7.9–7.4 (m, 2H, —CONHCH<, CH₃CONH-aryl); 4.2–0.8 (m, 20H, remaining H including 3.87, s, 3H, OCH₃ and 2.23, s, 3H, —COCH₃).

EXAMPLE 4

(±)
4-Amino-5-chloro-2-methoxy-N-(8β-1-aza-6α-H-4-oxabicyclo [4,4,0]delcyl)benzamide (4)

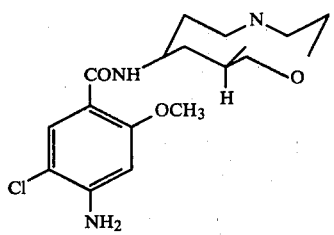

(3) (2.6 g) (prepared as in Example 3) was refluxed with an aqueous ethanol (water 5 ml, ethanol 50 ml) solution of potassium hydroxide (1 g) for 2 hours. On cooling, the ethanol was removed by rotary evaporation and the residue extracted with chloroform (2×50 ml) and dried ($K_2CO_3$). Filtration and removal of the solvent afforded the crude product, recrystallisation from ethyl acetatepetrol gave (±) 4-amino-5-chloro-2-methoxy-N-(8β-1-aza-6α-H-4-oxabicycl[4,4,0]decyl)-benzamide (4) (1.3 g, 55%) m.p. 195°-7°.

n.m.r. (δ, $CDCl_3$): 8.00 (s, 1H, aryl-6-H̲); 7.6-7.4 (m, 1H, —CONH̲—CH=); 6.23 (s, 1H, aryl 3-H); 4.6-1.0 (m, 19H, remaining proton including 3.83, s, 3H, —$OCH_3$).

EXAMPLE 5

(±)
4-Acetamido-5-chloro-2-methoxy-N-(8α-1-aza-2β-methyl-6α-H-4-oxabicyclo[4,4,0]decyl)benzamide (5)

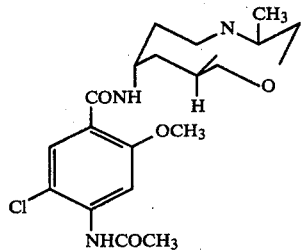

Following the procedures outline in Example 1, the (±) 8α-amino-1-aza-2β-methyl-6α-H-4-oxabicyclo[4,4,0]decane (D.12) (0.9 g) was converted to 4-acetamido-5-chloro-2-methoxy-N-(8α-1-aza-2β-methyl-6α-H-4-oxabicyclo [4,4,0]decyl)benzamide (5) (1.0 g, 47%) m.p. 165°-6°.

n.m.r. (δ, $CDCl_3$): 8.4-7.7 (m, 2H, —CONH̲—CH=, $CH_3$CONH̲); 8.28 (s, 1H, aryl-H̲); 8.14 (s, 1H, aryl-H̲); 5.65-4.2 (m, 1H, 8β-H̲); 4.2-3.0 (m, 8H including 4.0, s 3H, —$OCH_3$); 2.9-0.8 (m, 13H, including 2.27 s, 3H, —$COCH_3$) and 0.95, d, 3H, =CH—$CH_3$, J=6 Hz).

EXAMPLE 6

(±)
4-Amino-5-chloro-2-methoxy-N-(8α-1-aza-2β-methyl-6α-H-4-oxabicyclo[4,4,0]decyl)benzamide (6)

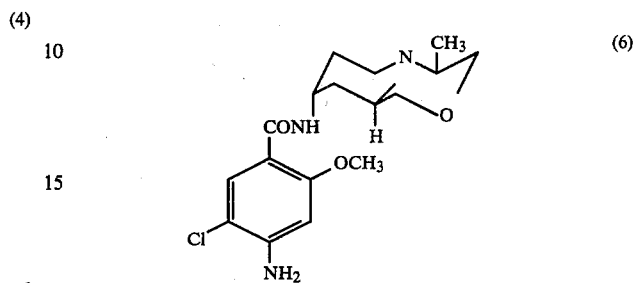

Following the procedures outlined in Example 4, the (±) 4-acetamido-5-chloro-2-methoxy-N-(8α-1-aza-2β-methyl-6α-H-4-oxabicyclo[4,4,0]decyl)benzamide (5) (1.0 g) was converted to (±) 4-amino-5-chloro-2-methoxy-N-(8α-1-aza-2β-methyl-6α-H-4-oxabicyclo[4,4,0]decyl)benzamide (6) (0.7 g, 80%). m.p. 221°-2°.

n.m.r. (δ, $CDCl_3$): 8.2-7.8 (m, 1H, —CONH̲—CH=); 7.96 (s, 1H, aryl 6-H); 6.24 (s, 1H, aryl 3-H); 4.8-2.9 (m, 11H includes 3.88, s, 3H, —$OCH_3$); 2.0-0.8 (m, 10H includes 0.96, d, 3H, >CH-$CH_3$, J=6 Hz).

EXAMPLE 7

(±)
4-Acetamido-5-chloro-2-methoxy-N-(8α,β-1-aza-6α-H-4-thiabicyclo[4,4,0]decyl)benzamide (7)

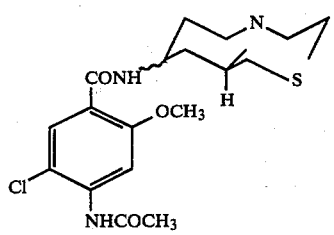

Following the procedures outlined in Example 1, the crude (±) 8α,β-amino-1-aza-6α-H-4-thiabicyclo[4,4,0]decane (D.17) (2.4 g) was converted to (±) 4-acetamido-5-chloro-2-methoxy-N-(8α,β-1-aza-6α-H-4-thiabicyclo[4,4,0]decyl)benzamide (7) (5.1 g, 90%). m.p. 185°-9° (EtoAc).

n.m.r. (δ,$CDCl_3$): 8.3-7.4 (m, 4H, aryl-H̲, —CONH̲C<, $CH_3$CONH̲-Aryl); 5.6-1.2 (m, 20H, includes 4.0, s, 2H, —$OCH_3$[α-isomer]; 3.9, s, 1H, —$OCH_3$[β-isomer]; 2.27, s, 3H, COCH̲$_3$).

EXAMPLE 8

(±) 4-Amino-5-chloro-2-methoxy-N-(8α-1-aza-6α-H-4-thiabicyclo [4,4,0]decyl)benzamide (8)

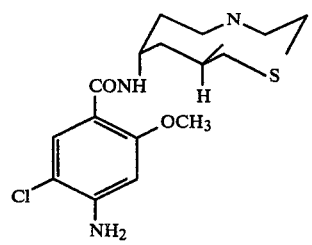

Following the procedures outlined in Example 4, the (±) 4-acetamido-5-chloro-2-methoxy-N-(8α,β-1-aza-6α-H-4-thiabicyclo[4,4,0]decyl)benzamide (7) (2.0 g) was converted to the crude (±) 4-amino-5-chloro-2-methoxy-N-(8α,β-1-aza-6α-H-4-thiabicyclo[4,4,0-]decyl)benzamide. Fractional recrystallisation from ethyl acetate afforded the pure (35) 4-amino-5-chloro-2-methoxy-N-(8α-1-aza-6α-H-4-thiabicyclo[4,4,0-]decyl)benzamide (8) (0.8 g, 45%). m.p. 183°-6°.

n.m.r. (δ, CDCl₃): 8.2–7.8 (m, 1H, >CONH—CH=); 8.05 (s, 1H, aryl 6-H); 6.27 (s, 1H, aryl 3-H); 4.1–4.6 (m, 3H, aryl-NH₂, 8β-H); 3.93 (s, 3H, —OCH₃); 3.4–1.4 (m, 13H, remaining protons).

EXAMPLE 9

(±) 4-Acetamido-5-chloro-2-methoxy-N-(8β-1-aza-6α-H-4-thiabicyclo [4,4,0]decyl)benzamide (9)

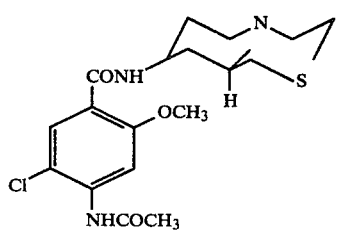

Following the procedures outlined in Example 1, the crude (±) 8β-amino-1-aza-6α-H-4-thiabicyclo[4,4,0]-decane) (D.20) (2.5 g) was converted to (±) 4-acetamido-5-chloro-2-methoxy-N-(8β-1-aza-6α-H-4-thiabicyclo[4,4,0]decyl benzamide (9) (2.2 g, 40%) m.p.=210°-3°.

n.m.r. (δ, CDCl₃): 8.25 (s, 1H, aryl H); 8.17 (s, 1H, aryl H); 8.0–7.5 (m, 2H, —CONH-CH>; CH₃CONH-aryl) 4.3–3.6 (m, 1H, - 8α-H); 3.9 (s, 3H, —OCH₃); 3.3–1.0 (m, 16H, remaining protons including 2.27, s, 3H, —COCH₃).

EXAMPLE 10

(±) 4-Amino-5-chloro-2-methoxy-N-(8β-aza-6α-H-4-thiabicyclo [4,4,0]decyl)benzamide (10)

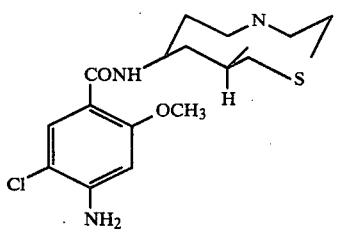

Following the procedures outlined in Example 4, the (±) 4-acetamido-5-chloro-2-methoxy-N-(8β-1-aza-6α-H-4-thiabicyclo[4,4,0]decyl)benzamide (9) (1.2 g) was converted to (±) 4-amino-5-chloro-2-methoxy-N-(8β-1-aza-6α-H-4-thiabicyclo[4,4,0]decyl)benzamide (10) (0.73 g, 65%). m.p. 206°-8°.

n.m.r. (δ, CDCl₃): 8.03 (s, 1H, aryl, 6H); 7.7–7.3 (m, 1H, >CONHCH=); 6.23 (s, 1H, aryl 3H); 4.6–3.7 (m, 6H, 8α-H, aryl NH₂ including 3.83, s, 3H, —OCH₃); 3.5–1.0 (m, 13H, remaining protons).

EXAMPLE 11

(±) 4-Acetamido-5-chloro-2-methoxy-N-(8α-1-aza-2β-phenyl-6α-H-4-oxabicyclo[4,4,0]decyl)benzamide (11)

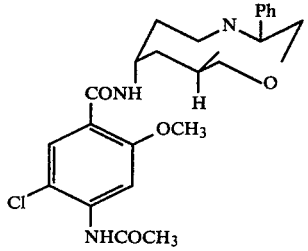

Following the procedures outlined in Example 1, the (±) 8α-amino-1-aza-2β-phenyl-6α-H-4-oxabicyclo[4,4,0]decane (D.23) (1.3 g) was converted to (±) 4-acetamido-5-chloro-2-methoxy-N-(8α-1-aza-2β-phenyl-6α-H-4-oxabicyclo[4,4,0]decyl)benzamide (11) (2.1 g, 80%) as an oil.

N.m.r. (δ, CDCl₃): 8.4–7.8 (m, 2H, CONH— and aryl-H); 8.23 (s, 1H, aryl-H); 8.08 (s, 1H, aryl-H); 7.6–6.9 (m, 5H, aryl-H); 4.5–1.0 (m, 19H, including 4.0, s, 3H—OCH₃, 2.3, s, 3H, —COCH₃).

EXAMPLE 12

(±)
4-Amino-5-chloro-2-methoxy-N-(8α-1-aza-2β-phenyl-6α-H-4-oxabicyclo[4,4,0]decyl)benzamide (12)

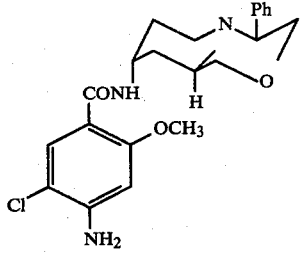

Following the procedures outlined in Example 4, the (±) 4-acetamido-5-chloro-2-methoxy-N-(8α-1-aza-2β-phenyl-6α-H-4-oxabicyclo[4,4,0]decyl)benzamide (11) (2.1 g) was converted to (±) 4-amino-5-chloro-2-methoxy-N-(8α-1-aza-2β-phenyl-6α-H-4-oxabicyclo[4,4,0]decyl)benzamide (12) (1.0 g, 50%), mp 145°–7°.

N.m.r. (δ, CDCl₃): 8.3–7.9 (m, 1H, —CON$\underline{H}$—CH= and s, 1H, aryl 6—$\underline{H}$); 7.6–6.9 (m, 5H, aryl-$\underline{H}$); 6.3 (s, 1H, aryl 3-$\underline{H}$); 4.7–3.1 (m, 11H, includes 3.93, s, 3H, —OC$\underline{H}$₃); 2.8–1.2 (m, 8H remaining C-H).

EXAMPLE 13

(±)
4-Acetamido-5-chloro-2-methoxy-N-(8β-1-aza-2β-phenyl-6α-H-4-oxabicyclo[4,4,0]decyl)benzamide (13)

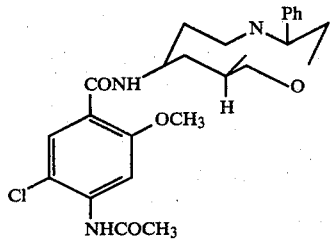

Following the procedures outlined in Example 1, the (±) 8β-amino-1-aza-2β-phenyl-6α-H-4-oxabicyclo[4,4,0]decane (D.26) (2.1 g) was converted to (±) 4-acetamido-5-chloro-2-methoxy-N-(8β-1-aza-2β-phenyl-6α-H-4-oxabicyclo[4,4,0]decyl)benzamide (13) (3.2 g, 75%) as an oil.

N.m.r. (δ, CDCl₃): 8.4–7.5 (m, 2H, —CON$\underline{H}$—CH=, CH₃CON$\underline{H}$—); 8.25 (s, 1H, aryl-$\underline{H}$); 8.10 (s, 1H, aryl-$\underline{H}$); 7.4–7.2 (m, 5H, aryl-$\underline{H}$); 4.7–1.0 (m, 19H, including s, 3H, 3.88, —OC$\underline{H}$₃; s, 3H, 2.22, —COC$\underline{H}$₃).

EXAMPLE 14

(±)
4-Amino-5-chloro-2-methoxy-N-(8β-1-aza-2β-phenyl-6α-H-4-oxabicyclo[4,4,0]decyl)benzamide monohydrate (14)

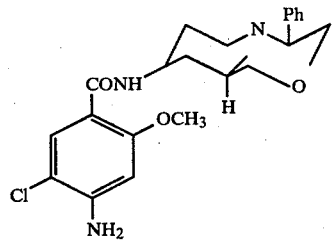

Following the procedures outlined in Example 4, the (±) 4-acetamido-5-chloro-2-methoxy-N-(8β-1-aza-2β-phenyl-6α-H-4-oxabicyclo[4,4,0]decyl)benzamide (13) (3.2 g) was converted to (±) 4-amino-5-chloro-2-methoxy-N-(8β-1-aza-2β-phenyl-6α-H-4-oxabicyclo[4,4,0]decyl)benzamide monohydrate (14) (1.6 g, 50%) mp 138°–45°.

N.m.r.: 8.07 (s, 1H, aryl 6-$\underline{H}$); 7.7–7.2 (m, 6H, —CON$\underline{H}$—CH= and aryl —$\underline{H}$); 6.28 (s, 1H, aryl 3-$\underline{H}$); 4.6–1.0 (m, 20H, includes 3.86, s, 3H, —OC$\underline{H}$₃).

EXAMPLE 15

(±)
4-Acetamido-5-chloro-2-methoxy-N-(8α,β-1-aza-6α-H-4-oxothiabicyclo[4,4,0]decyl)benzamide (15)

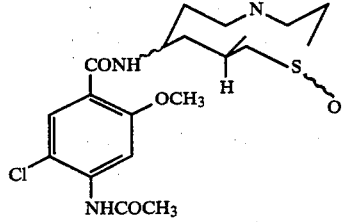

To a stirred solution of (±) 4-acetamido-5-methoxy-N-(8α,β-1-aza-6α-H-4-thiabicyclo[4,4,0-]decyl)benzamide (7) (2.0 g) in methanol (50 ml) was added a solution of sodium periodate (1.5 g) dissolved in the minimum quantity of water, and the resulting reaction mixture stirred at room temperature for 3 hours.

The solvent was removed in vacuo, water (10 ml) added, followed by chloroform (100 ml). Separation of the organic layer gave, on concentration and drying, (±) 4-acetamido-5-chloro-2-methoxy-N-(8α,β-1-aza-6α-H-4-oxothiabicyclo[4,4,0]decyl)benzamide (15) (2.1 g, 100%) as a foam.

N.m.r. (δ, CDCl₃): 8.2–7.5 (m, 2H, —CON$\underline{H}$—); 8.43 (br.s, 1H, aryl-$\underline{H}$); 8.27 (br.s, 1H, aryl-$\underline{H}$); 4.8–1.1 (m, 20H, including 3 singlets, 3H, —OC$\underline{H}$₃; 4.03, 4.00, 3.95, 2.3, s, 3H, —COC$\underline{H}$₃).

EXAMPLE 16

(±) 4-Amino-5-chloro-2-methoxy-N-(8α,β-1-aza-6α-H-4-oxothiabicyclo[4,4,0]decyl)benzamide (16)

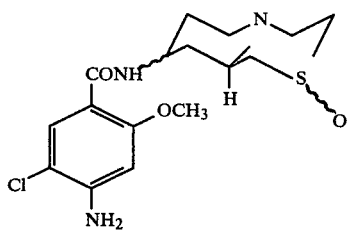

Following the procedures outlined in Example 4, the (±) 4-acetamido-5-chloro-2-methoxy-N-(8α,β-1-aza-6α-H-4-oxothiabicyclo[4,4,0]decyl)benzamide (15) (2.1 g) was converted into (±) 4-amino-5-chloro-2-methoxy-N-(8α,β-1-aza-6α-H-4-oxothiabicyclo[4,4,0-]decyl)benzamide (1.0 g, 50%), mp 130°–8°.

N.m.r. (δ, CDCl$_3$): 8.3–7.4 (m, 1H, —CONH—CH=); 8.06 (br.s, 1H, aryl 6-H); 6.30 (br.s, 1H, aryl 3-H); 4.7–1.1 (m, 19H, includes 3.94, 3.91, 3.87, 3 singlets, 3H—OCH$_3$).

EXAMPLE 17

(±) 4-Acetamido-5-chloro-2-methoxy-N-(8β-1-aza-6α-H-4-oxothiabicyclo[4,4,0]decyl)benzamide (17)

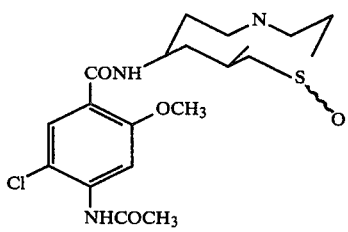

Following the procedures outlined in Example 15, the (±) 4-acetamido-5-chloro-2-methoxy-N-(8β-1-aza-6α-H-4-thiabicyclo[4,4,0]decyl)benzamide (9) (1.1 g) was converted to (±) 4-acetamido-5-chloro-2-methoxy-N-(8β-1-aza-6α-H-4-oxothiabicyclo[4,4,0]decyl)benzamide (17) (0.9 g, 80%). mp 245°–6° (dec).

N.m.r. (δ, CDCl$_3$): 8.25 (s, 1H, aryl-H); 8.15 (s, 1H, aryl-H); 7.95–7.45 (m, 2H, —CONH—); 4.3–1.1 (m, 20H, including 3.95, s, 3H, —OCH$_3$; 2.3, s, 3H, —COCH$_3$).

EXAMPLE 18

(±) 4-Amino-5-chloro-2-methoxy-N-(8β-1-aza-6α-H-4-oxothiabicyclo[4,4,0]decyl)benzamide (18)

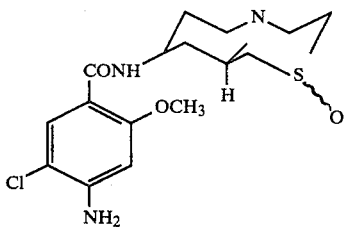

Following the procedures outlined in Example 4, the (±) 4-acetamido-5-chloro-2-methoxy-N-(8β-1-aza-6α-H-4-oxathiabicyclo[4,4,0]decyl)benzamide (17) (0.9 g) was converted to (±) 4-amino-5-chloro-2-methoxy-N-(8β-1-aza-6α-H-4-oxathiabicyclo[4,4,0]decyl)benzamide (18) (0.4 g, 50%). mp 209°–11°.

N.m.r. (δ, CDCl$_3$): 8.06 (s, 1H, aryl 6-H); 7.8–7.4 (m, 1H, —CONH—CH=); 6.30 (s, 1H, aryl 3-H); 4.7–1.1 (m, 19H, inlcudes 3.87, s, 3H, —OCH$_3$).

EXAMPLE 19

(±) 2-Methoxy-5-sulphonamido-N-(8β-1-aza-6α-H-4-thiabicyclo[4,4,0]decyl)benzamide (19)

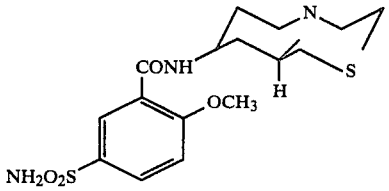

To a solution of 2-methoxy-5-sulphonamido benzoic acid (1.8 g) in dry DMF (30 ml) at 0° C. was added, dropwise, a solution of oxalyl chloride (0.68 ml) in chloroform (5 ml) over 20 minutes. On stirring for a further 30 minutes, a solution of triethylamine (3 ml) in chloroform (5 ml) followed by ±8β-amino-1-aza-6α-H-4-thiabicyclo[4,4,0]decane (D 20) (1.2 g) in chloroform (5 ml) was added and the whole stirred for a further 2 hours at room temperature. Water (10 ml) followed by saturated potassium carbonate solution was added and the organic phase separated and the aqueous phase extracted with chloroform (2×100 ml), dried (K$_2$CO$_3$) and the solvent removed to yield an oil. Purification by column chromatography (Alumina+10% water; chloroform+2% methanol) gave the (±) 2-methoxy-5-sulphonamido-N-(8β-1-aza-6α-H-4-thiabicyclo[4,4,0-]decyl)benzamide (19) (0.3 g, 11%), mp 216°–8° (ethyl acetate).

N.m.r. (δ, CDCl$_3$): 8.62 (d, 1H, J=2.5 Hz, aryl 6-H); 7.98 (d,d, 1H, J=2.5, 8.7 Hz, aryl 4-H); 7.7–7.57 (m, 1H, CONH—); 7.06 (d, 1H, J=8.7 Hz, aryl 3-H); 6.7–6.25 (m, 2H, —SO$_2$NH$_2$); 4.5–3.7 (m, 4H, CONHCH> including 4.0, s, 3H, —OCH$_3$); 3.4–1.0 (m, 13H, remaining protons).

EXAMPLE 20

(±) 2,4-Dimethoxy-N-(8β-1-aza-6α-H-4-thiabicyclo[4,4,0-]decyl)benzamide (20)

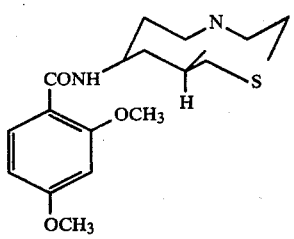

To a stirred solution of 2,4-dimethoxybenzoic acid (1.1 g) in $CH_2Cl_2$ (100 ml) was added oxalyl chloride (0.48 ml) and DMF (ca 5 drops) and the whole stirred until gas evolution ceased (ca 1 hour). The reaction mixture was cooled to 0° C. and triethylamine (2 ml) in $CH_2Cl_2$ (10 ml) followed by (±) 8β-amino-1-aza-6α-H-4-thiabicyclo[4,4,0]decane (D 20) (0.85 g) in $CH_2Cl_2$ (10 ml) added and the whole stirred at room temperature for 2 hours. Aqueous sodium hydroxide (2.5 N, 10 ml) was added and the organic layer separated, dried ($K_2CO_3$) and evaporated to give an oil, which was purified by chromatography (Alumina+10% water; $CH_2Cl_2$) to give (±) 2,4-dimethoxy-N-(8β-1-aza-6α-H-4-thiabicyclo[4,4,0]decyl)benzamide (20) (1.08 g, 65%), mp 130°-2° (EtOAc/Petrol).

N.m.r. (δ, $CDCl_3$): 8.15 (d, 1H, J=8.6 Hz, aryl 6H); 7.75–7.45 (m, 1H, CONH); 6.59 (d,d, 1H, J=8.6 Hz, 2.3 Hz, aryl 5-H); 6.47 (d, 1H, J=2.3 Hz, aryl 3H); 4.8–3.7 (m, 7H, CONHCH= including 3.90, s, 3H, —OCH₃ and 3.84, s, 3H, OCH₃); 3.25–1.0 (m, 13H, remaining protons).

EXAMPLE 21

(±) 4-Chloro-2-methoxy-N-(8β-1-aza-6α-H-4-thia-bicyclo[4,4,0]decyl)benzamide (21)

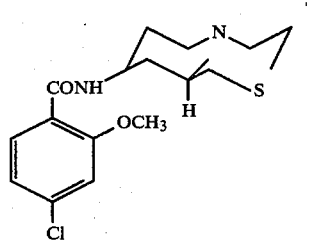

Following the procedures detailed in Example 20, the (±) 8β-amino-1-aza-6α-H-4-thiabicyclo[4,4,0]decane (D 20) (0.85 g) was converted to (±) 4-chloro-2-methoxy-N-(8β-1-aza-6α-H-4-thiabicyclo[4,4,0]decyl)-benzamide (21) (1.0 g, 60%), mp=145°-7° (E tOAc)-/petrol).

N.m.r. (δ, $CDCl_3$): 8.12 (d, 1H, J=8.3 Hz, aryl 6H); 7.75–7.4 (m, 1H, —CONH); 7.12.6.93 (m, 2H, aryl 5H, 3H); 4.3–3.75 (m, 4H, CONHCH= including 3.93, s, 3H, OCH₃); 3.25–1.0 (m, 13H, remaining protons).

Biological Data Section

Gastric Activity

Increase in intragastric pressure in the rat

Intragastric pressure changes were recorded from previously starved conscious but retrained rats using a saline filled catheter inserted into the lumen of the stomach via a permanent gastric fistula. The catheter was connected to a physiological pressure transducer and pressure changes recorded on a hot wire pen recorder. In each animal pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for the 40 minute period after the subcutaneous administration of the compounds. Students 't' test was applied to the difference in average values obtained for spontaneous and post-compound activity.

Table I shows the minimum dose for activity.

TABLE I

| Compound of Example No. | Dose mg/kg Subcutaneously | Orally |
|---|---|---|
| 2 | 0.5 | 0.5 |
| 4 | 1.0 | n.t. |
| 6 | 0.2 | 0.5 |
| 8 | 5.0 | n.t. |
| 10 | 1.0 | n.t. |
| 14 | 1 | n.t. |
| 16 | 5 | n.t. |
| 18 | 1 | n.t. | n.t. = not tested

Compounds were also tested for their ability to inhibit apomorphine induced climbing in the mouse. Inactivity in this test may be indicative of a low propensity to produce extra-pyramidal side-effects in man. The results are shown in the Table 2 below:

The method used for this test is as set out below:

TABLE 2

| Compound of Example No | Dose mg/kg ED₅₀ |
|---|---|
| 2 | 70 |
| 4 | 30 |
| 6 | 40 |
| 8 | Ia at 25 |
| 12 | 30 |
| 14 | Ia at 10 po |
| 16 | Ia at 10 po |

Inhibition of apomorphine induced climbing in the mouse

The test is based on that described by Protais, P., Constantin, J. and Schwartz, J. C. (1976), Psychopharmacology, 50, 1–6.

Apomorphine 1 mg/kg s.c. induces mice to climb the wall of a wire cage (inverted food hopper—11×7.5×18 cm high). Mice acclimatised in their home cages in groups of 5 are placed under the hoppers immediately after the injection of apomorphine 1 mg/kg s.c. At 10, 20 and 30 minutes after injection climbing behaviour is scored. The mice are observed for 30 seconds and scored according to the position in which they spend the majority of time, score 0—four paws on floor of cage; score 1—fore paws only on walls; score 2—all paws on wall of cage.

The scores at all 3 times for each mouse are summed for apomorphine only and for apomorphine plus compound groups of mice.

Total scores are then calculated as the percentage inhibition of climbing as follows:

% Inhibition = $100 - \left[\dfrac{\text{Total scores of drug treated group}}{\text{Total scores of apomorphine only group}}\right] \times 100$ From graphical representation of the results $ED_{50}$ values (the dose that inhibits the apomorphine response by 50%) are then obtained.

Toxicity

No toxic effects were observed in these tests.

We claim:

1. A compound of the formula (I):

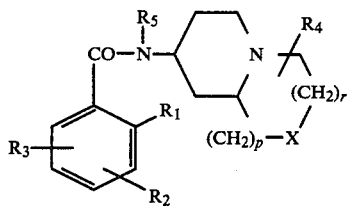

and pharmaceutically acceptable salts and N-oxides thereof, wherein:

$R_1$ is a $C_{1-6}$ alkoxy group;

$R_2$ and $R_3$ are the same or different and are hydrogen, halogen, $CF_3$, $C_{1-7}$acyl, $C_{1-7}$ acylamino, $C_{1-6}$ alkyl-$S(O)_n$ wherein n is 0, 1 or 2, nitro, $C_{1-6}$ alkoxy, hydroxy, or amino, aminocarbonyl or aminosulphonyl optionally substituted by one or two $C_{1-6}$ alkyl groups;

or $R_1$ and $R_2$ taken together are methylenedioxy or ethylenedioxy in which case $R_3$ is any one of the groups given for $R_1$ and $R_2$ above;

$R_4$ is hydrogen, $C_{1-4}$ alkyl, phenyl or phenyl $C_{1-4}$ alkyl;

$R_5$ is hydrogen or $C_{1-4}$ alkyl;

X is oxygen atom;

p is 1; and r is 1.

2. A compound according to claim 1, wherein $R_2$ and $R_3$ are as defined except that when alkyl-$S(O)_n$, n must be 2, and X is oxygen.

3. A compound according to claim 1, wherein the benzamide moiety has the structure (III):

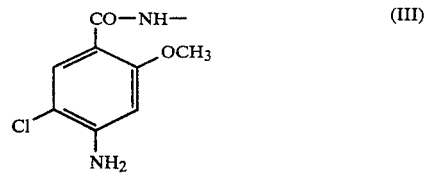

4. A compound according to claim 1, wherein the bicyclic moiety has the structure (V):

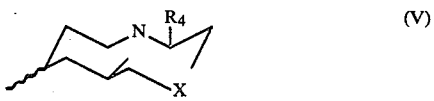

5. A compound according to claim 1, of formula (VI):

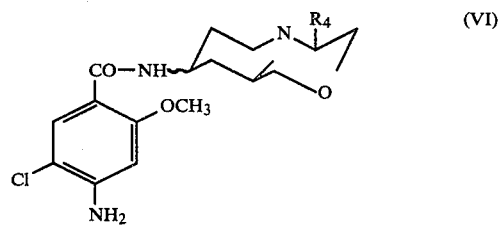

6. A compound according to claim 1, wherein $R_4$ is hydrogen or methyl.

7. A compound according to claim 1, having an axial bond between the amide nitrogen and the ring carbon to which it is bound.

8. A pharmaceutical composition comprising a compound according to claim 1 in an amount effective for the treatment of disorders related to impaired gastrointestinal motility, together with a pharmaceutically acceptable carrier.

9. A compound according to claim 1, for use in the treatment of disorders related to impaired gastro-intestinal motility including retarded gastric emptying, dyspepsia, flatulence, oesophagal reflux, peptic ulser and emesis and which compound is a dopamine antagonist.

* * * * *